US00PP15516P2

(12) United States Plant Patent
Trees

(10) Patent No.: US PP15,516 P2
(45) Date of Patent: Feb. 1, 2005

(54) ***LANTANA* PLANT NAMED 'BALANDPAWN'**

(50) Latin Name: *Lantana camara*
Varietal Denomination: Balandpawn

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 11 days.

(21) Appl. No.: 10/741,701

(22) Filed: Dec. 19, 2003

(51) Int. Cl.[7] ..... A01H 5/00
(52) U.S. Cl. ..... Plt./227
(58) Field of Search ..... Plt./227

(56) References Cited

PUBLICATIONS

UPOV ROM GTITM Computer Database, GTI Jouve Retrieval Software 2004/02 Citation for 'Balandpawn'.*

* cited by examiner

*Primary Examiner*—Kent Bell
*Assistant Examiner*—W C Haas
(74) *Attorney, Agent, or Firm*—Wood, Phillips, Katz, Clark & Mortimer

(57) ABSTRACT

A new and distinct *Lantana* plant named 'Balandpawn', characterized by its flowers ranging from yellow-colored when first open to pink-colored when fully mature, dark green-colored foliage, and upright and mounded growth habit.

1 Drawing Sheet

Latin name of genus and species of plant claimed: *Lantana camara.*
Variety denomination: 'Balandpawn'.

BACKGROUND OF THE INVENTION

The present invention relates to a new and distinct cultivar of *Lantana* plant botanically known as *Lantana camara* and hereinafter referred to by the cultivar name 'Balandpawn'.

The new cultivar was developed by the inventor in a controlled breeding program during April 1999, at Arroyo Grande, Calif. The objective of the breeding program was the development of *Lantana* cultivars with a well-branched, compact habit, continuous flowering and dark green-colored foliage.

The new cultivar was the product of the self-pollination of the commercially available *Lantana* cultivar 'Good Sonne' (not patented), characterized by its gold-colored flowers, medium green-colored foliage, and compact upright growth habit. 'Balandpawn' was selected in May 2000 as a single flowering plant within the progeny of the above stated self-pollination and was initially designated '59-2'.

Asexual reproduction of the new cultivar by terminal stem cuttings taken since May 2000 at Arroyo Grande, Calif. and West Chicago, Ill. has demonstrated that the new cultivar reproduces true to type, with all the characteristics as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits flowers ranging in color from pale yellow when first open to light pink at full maturity.

2. Forms dark green-colored foliage, and
3. Exhibits an upright and mounded growth habit.

Plants of the new cultivar differ from plants of the parent cultivar primarily in flower color, foliage size, and growth habit.

Plants of the new cultivar can be compared to plants of the *Lantana* cultivar 'Pink Caprice' (unpatented). However, in side-by-side comparisons, plants of the new cultivar differ from plants of the cultivar 'Pink Caprice' in the following characteristics:

1. Plants of the new cultivar are shorter than plants of the cultivar 'Pink Caprice', and
2. Plants of the new cultivar are more floriferous than plants of the cultivar 'Pink Caprice'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balandpawn'. The plants were grown for 10 weeks in a greenhouse at West Chicago, Ill.

DETAILED BOTANICAL DESCRIPTION

Figure 1:
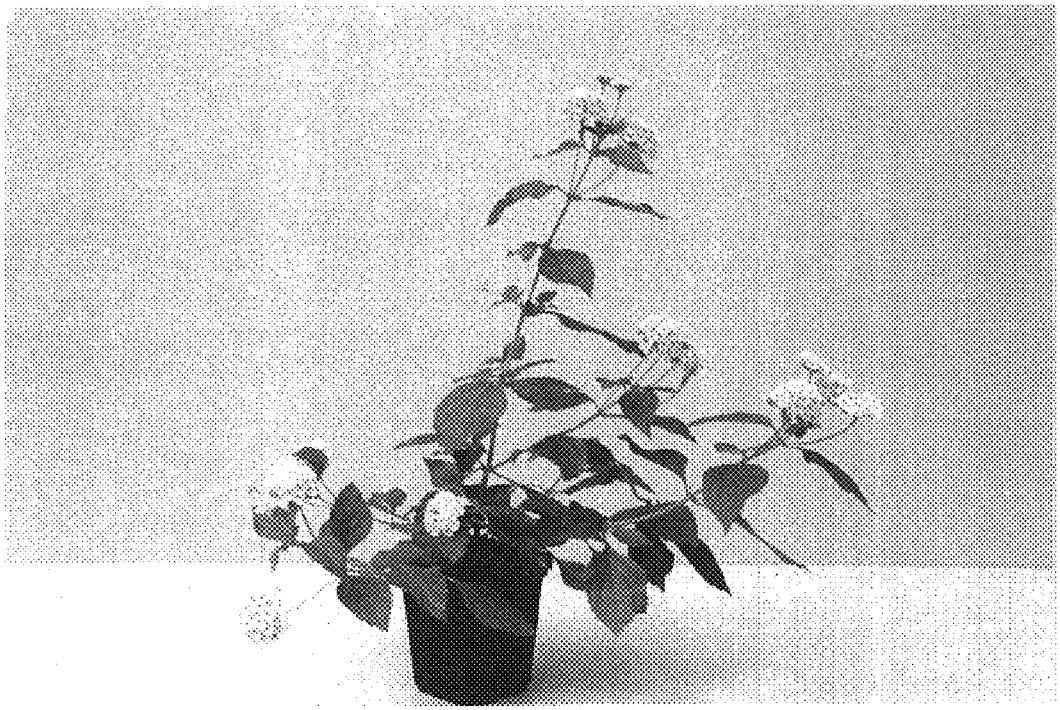
FIG. 1 illustrates a side view of the overall growth and flowering habit of 'Balandpawn'.
Figure 2:
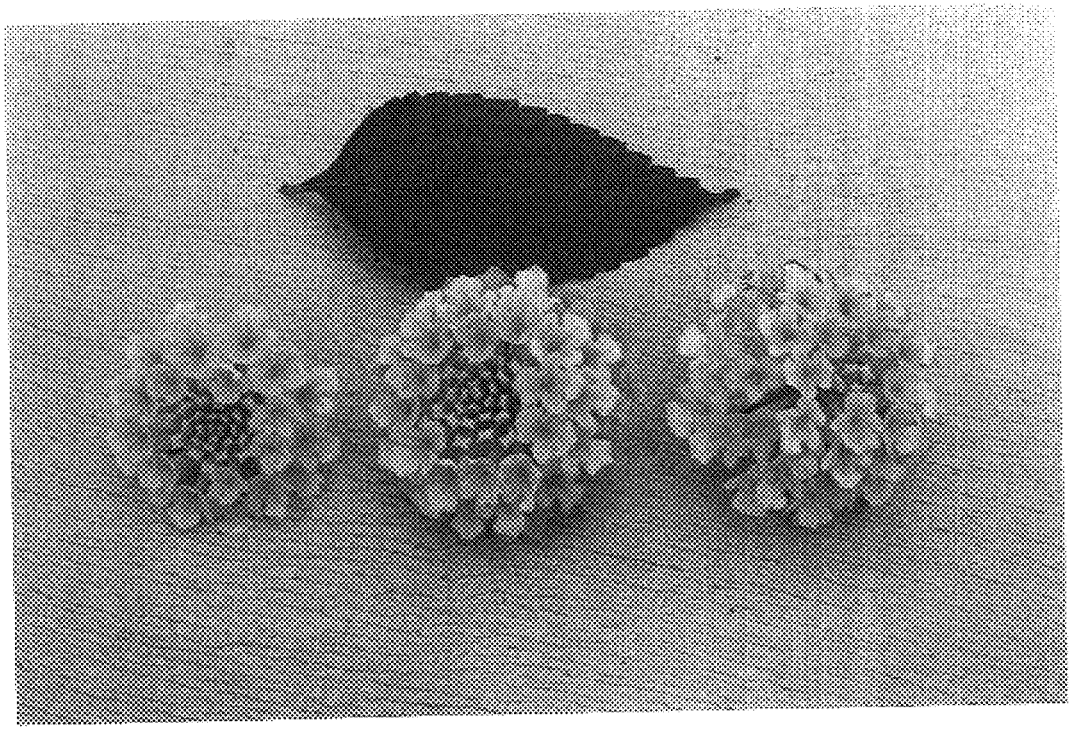
FIG. 2 illustrates a close-up view of three inflorescences of 'Balandpawn' showing flowers ranging in color from yellow when first open to pink at full maturity.

The chart used in the identification of colors described herein is the R.H.S. Colour Chart of The Royal Horticultural Society, London, England, 1995 edition, except where general color terms of ordinary significance are used. The color values were determined on Jul. 21, 2003. The readings were taken between 9:00 and 11:00 a.m. under natural day light conditions. The plants were produced from terminal stem cuttings taken from stock plants and were grown in a double polycarbonate-covered greenhouse under conditions comparable to those used in commercial practice. The plants were grown in 10 cm pots for 10 weeks while utilizing a soilless growth medium in a greenhouse at West Chicago, Ill. Greenhouse temperatures were maintained at approximately 75°–85° F. (24°–29° C.) during the day and approximately 62°–68° F. (17°–20° C.) during the night. Greenhouse light levels were maintained at 4,000–10,000 footcandles during the day.

Botanical classification: *Lantana camara* cultivar 'Balandpawn'.

Parentage: Self-pollination of the *Lantana* cultivar 'Gold Sonne' (not patented).

Propagation:

*Type cutting.*—Terminal stem cutting.

*Time to initiate roots.*—Approximately 7 to 11 days.

*Time to develop roots.*—Approximately 4 weeks.

*Root description.*—Fine, fibrous.

*Rooting habit.*—Freely branching.

Plant description:

*Habit of growth.*—Vigorous. Forms lateral branches at every node. Pinching enhances basal branching. A mature plant, 10 weeks after the planting of a rooted cutting, measures approximately 26.8 cm in height from soil level to top of plant plane and approximately 39 cm in diameter (area of spread) with 4.2 main branches.

*Form.*—Upright, mounded and spreading.

*Branch.*—Shape: Quadrilateral. Strength: Strong. Length: Approximately 23.8 cm. Diameter: Approximately 3 mm. Texture: Moderately pubescent with short stiff hairs. Color of young supple branch: 144A. Color of mature woody branch: N199A. Internode length at middle of stem is approximately 5.3 cm.

*Foliage.*—Type: Simple. Arrangement: Opposite. Orientation to stem: 90° angle. Fragrance: Faint, spicy. Shape: Ovate. Margin: Crenate. Apex: Acute. Base: Cuneate. Texture of upper surface: Moderately pubescent. Texture of lower surface: Densely covered with short, stiff hairs. Leaf length: Approximately 7.6 cm. Leaf width: Approximately 4.6 cm. Venation pattern: Pinnate. Color of upper surface of mature foliage: Closest to 139A with veins of 145C. Color of lower surface of mature foliage: 147B with veins of 145C. Petiole length: Approximately 1 cm. Petiole diameter: Approximately 2 mm. Petiole texture: Upper surface: Moderately covered with short, stiff hairs. Lower surface: Dense stiff hairs with moderate amount of glandular pubescence. Petiole color of both surfaces: Lighter than 147C.

Flowering description:

*Flowering habit.*—Freely flowering.

*Natural flowering season.*—Year round in greenhouse environment and spring through autumn in outdoor garden.

Inflorescence description:

*Type.*—Corymb.

*Shape.*—Spherical.

*Size.*—Depth (height): Approximately 2 cm. Diameter: Approximately 3.9 cm. Number of florets per inflorescence: Approximately 37 fully open flowers at any one time.

*Bract.*—Each flower is subtended by a single bract. Bract: Shape: Lanceolate. Length: Approximately 6 mm. Width: Approximately 1 mm. Apex: Acute. Margin: Entire. Texture: Lower surface is densely pubescent, upper surface is slightly pubescent with short hairs. Color of both surfaces: 143B at base, 137C at apex.

*Peduncle.*—Shape: Quadrilateral. Length: Approximately 8.5 cm. Diameter: Approximately 1 mm. Aspect: At acute angle to branch. Texture: Pubescent with short stiff hairs. Color: 144A.

Flower description:

*Shape.*—Salverform.

*Fragrance.*—Light, sweet.

*Aspect.*—Concave.

*Lastingness of bloom.*—Approximately 8 days from first color on outer buds to dropping of last flower.

*Bud.*—Shape: Roughly spherical. Length: Approximately 3 mm. Width: Approximately 3 mm. Color: 15A.

*Corolla size.*—Diameter: Approximately 1.1 cm.

*Petals.*—Five, non imbricate, non-symmetrical, fused at base forming corolla tube. Petal shape: Obovate. Petal apex: Obtuse. Petal margin: Entire, slightly ruffled. Petal texture: Moderate pubescence at base only. Upper petal length from throat: Approximately 3.6 mm. Upper petal width: Approximately 4 mm. Lateral petal length from throat: Approximately 3.6 mm. Lateral petal width: Approximately 5 mm. Lower petal length from throat: Approximately 3.6 mm. Lower petal width: Approximately 6.3 mm. Petal color when first open: Upper surface: 155B with 17C around throat opening. Lower surface: 75C. Petal color when fully open: Upper surface: 75C at margin, 23A around throat opening. Lower surface: 75C. Petal color when fully mature: N74D with N74B around throat opening. Lower surface: 75C.

*Corolla tube.*—Length: Approximately 1.2 cm. Diameter at tube opening: Approximately 1.5 mm. Diameter at base: Approximately 1 mm. Texture of outer surface of tube: Densely covered with short hairs. Texture of inner surface: Glabrous except for hairs around opening. Color of both inner and outer surface: First open: Ranging from 10C at distal end to 15D at proximal end. Fully open: Ranging from 155D at distal end to 65D at proximal end.

*Calyx.*—Shape: Tubular. Length: Approximately 2 mm. Diameter: Approximately 1 mm. Apex: Obtuse. Texture: Densely pubescent. Color: 145C.

*Reproductive organs.*—Stamens: Four per flower, adnate to the corolla tube. Filament length of free portion: Approximately 2 mm. Filament color: 155D. Anther shape: 2 lobed, lanceolate. Anther length: 1 mm. Anther color: Closest to 199C. Amount of pollen: None observed. Pistil quantity: One per flower. Pistil length: 4 mm. Stigma shape: Oval. Stigma length: 1 mm. Stigma color is N144A. Style length: Approximately 2 mm. Style color: 145C. Ovary length: 1 mm. Ovary color: N144B.

Seed and fruit production: Neither seed nor fruit production has been observed.

Disease and pest resistance: Resistance to pathogens or pests common to *Lantana* has not been observed.

Hardiness zone: 'Balandpawn' is hardy in zones nine (9) and above.

What is claimed is:

1. A new and distinct cultivar of *Lantana camara* plant named 'Balandpawn' substantially, as herein shown and described, which:

1. Exhibits flowers ranging from yellow-colored when first open to pink-colored when fully mature,
2. Forms dark green-colored foliage, and
3. Exhibits an upright and mounded growth habit.

* * * * *